(12) United States Patent
Kaneko

(10) Patent No.: US 7,114,848 B2
(45) Date of Patent: Oct. 3, 2006

(54) ENVIRONMENT SENSOR

(75) Inventor: Norio Kaneko, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 126 days.

(21) Appl. No.: 10/887,274

(22) Filed: Jul. 8, 2004

(65) Prior Publication Data

US 2005/0008061 A1    Jan. 13, 2005

(30) Foreign Application Priority Data

Jul. 10, 2003   (JP)   ............................. 2003-273036
May 18, 2004   (JP)   ............................. 2004-148034

(51) Int. Cl.
*G01K 13/00*   (2006.01)

(52) U.S. Cl. ................ 374/142; 73/335.04; 73/335.05; 374/16; 374/28; 374/184; 374/109

(58) Field of Classification Search ................ 374/142, 374/16, 28, 184, 109; 73/335.05, 335.04, 73/73; 324/142
See application file for complete search history.

(56) References Cited

U.S. PATENT DOCUMENTS

| | | | |
|---|---|---|---|
| 3,703,696 A * | 11/1972 | Browall et al. ................ 338/35 |
| 4,217,623 A * | 8/1980 | Nishino et al. ............. 361/280 |
| 4,379,406 A * | 4/1983 | Bennewitz et al. ...... 73/335.02 |
| 4,393,434 A * | 7/1983 | Imai et al. ................... 361/286 |
| 4,419,021 A * | 12/1983 | Terada et al. ................ 374/101 |
| 4,649,364 A * | 3/1987 | Tanahashi et al. ............ 338/14 |
| 4,677,416 A * | 6/1987 | Nishimoto et al. ........... 338/35 |
| 4,899,549 A * | 2/1990 | Berge et al. ................... 62/160 |
| 5,969,639 A * | 10/1999 | Lauf et al. ............. 340/870.17 |
| 6,229,318 B1 * | 5/2001 | Suda .......................... 324/696 |
| 6,883,371 B1 * | 4/2005 | Sugaya et al. ........... 73/335.05 |
| 7,032,448 B1 * | 4/2006 | Hamamoto ............. 73/335.04 |
| 2003/0002238 A1* | 1/2003 | Toyoda ....................... 361/302 |
| 2003/0214310 A1* | 11/2003 | McIntosh ..................... 324/658 |

FOREIGN PATENT DOCUMENTS

| | | |
|---|---|---|
| EP | 1 179 825 A2 | 2/2002 |
| GB | 2 322 452 | 8/1998 |
| JP | 54102146 * | 8/1979 ................. 374/142 |
| JP | 54102148 * | 8/1979 ................. 374/142 |
| JP | 55155239 | 3/1980 |
| JP | 5-149901 | 6/1993 |
| JP | 6-242048 | 9/1994 |
| JP | 2002-90329 | 3/2002 |

* cited by examiner

*Primary Examiner*—Gail Verbitsky
*Assistant Examiner*—Megann E Vaughn
(74) *Attorney, Agent, or Firm*—Morgan & Finnegan, LLP

(57) ABSTRACT

An environment sensor (11) for measuring the temperature and humidity can be miniaturized and can respond at high speed. The environment sensor (11) includes a temperature sensing portion (111) having a temperature-sensitive material (1) made of a metal oxide, and a humidity-sensing portion (112) which is formed on the same substrate as the temperature sensing portion (111) and measures the ambient humidity by using a change in electrical characteristics. At least one of a pair of electrodes (2, 3) of the temperature sensor (111) is integrated with an electrode of the humidity-sensing portion (112).

6 Claims, 10 Drawing Sheets

HUMIDITY SENSING PORTION    TEMPERATURE SENSING PORTION

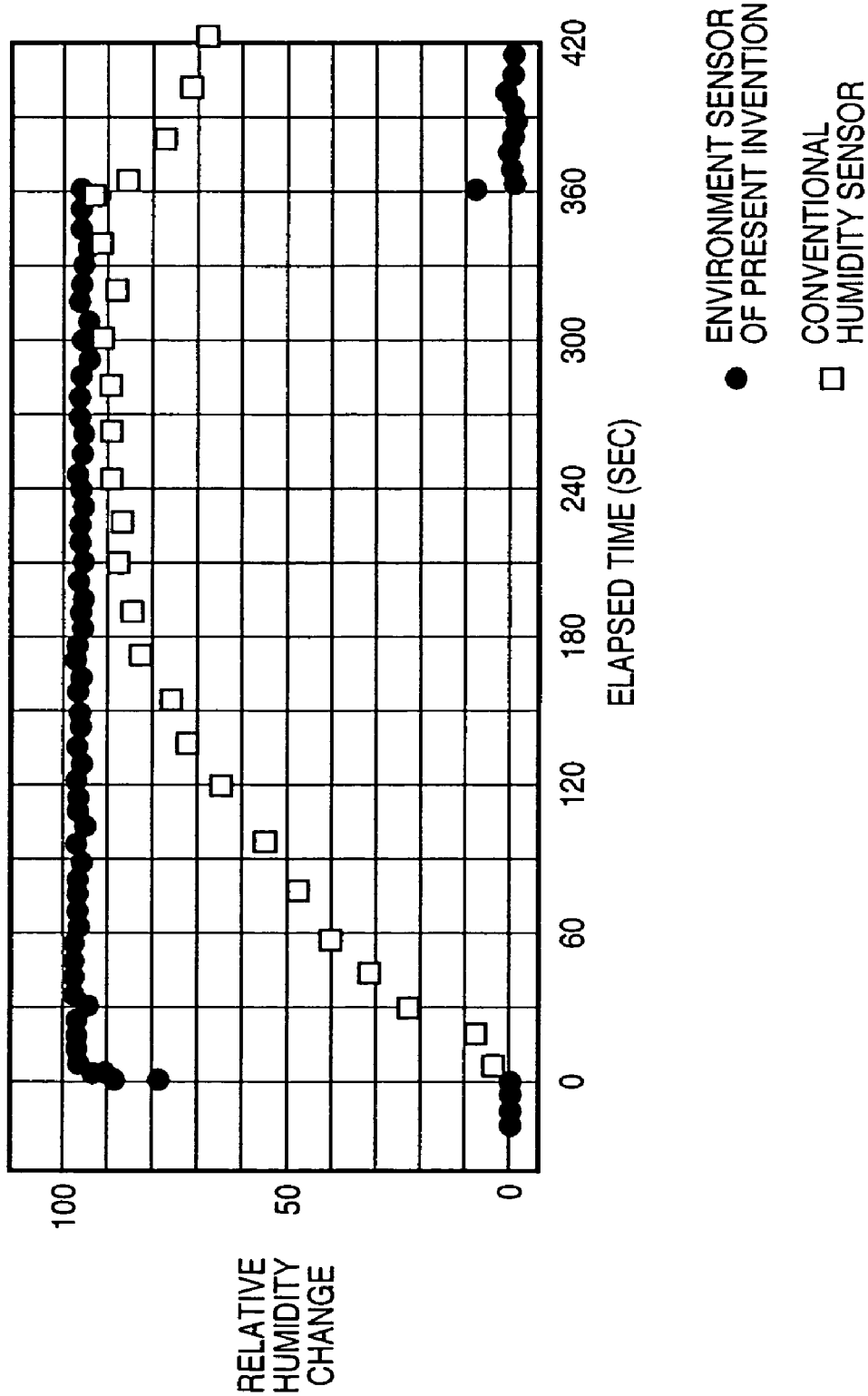

F I G. 10
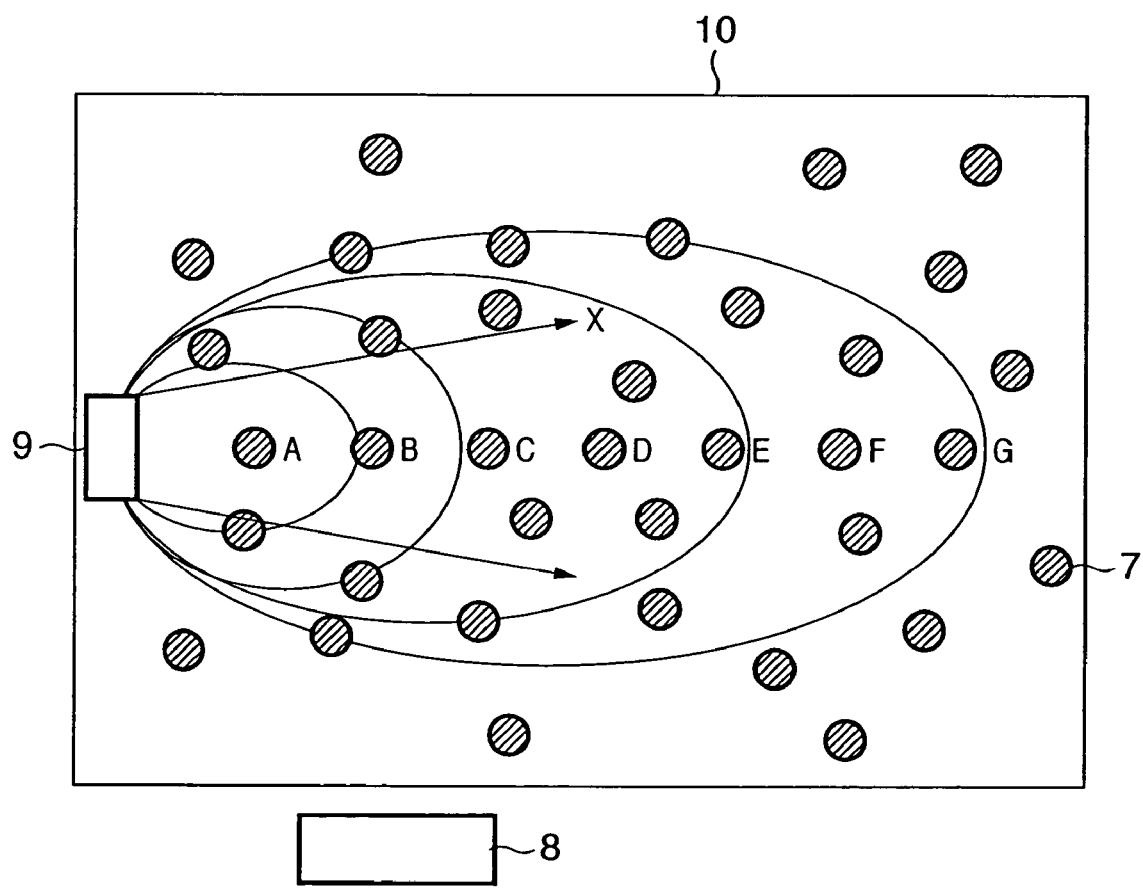

ENVIRONMENT SENSOR

FIELD OF THE INVENTION

The present invention relates to an environment sensor for measuring the temperature and humidity, an environment measurement apparatus including the environment sensor, and an environment measurement system having the environment measurement apparatus.

BACKGROUND OF THE INVENTION

Environment sensors for measuring the temperature and humidity have been conventionally put into practical use. These environment sensors are widely used in, e.g., food processors such as microwave ovens, household electric products such as air-conditioners, business machines such as copying machines, cooling water temperature monitors of automobiles, various types of air-conditioners, and weather observation.

Generally, an environment sensor individually measures the temperature and humidity. Japanese Patent Laid-Open No. 2002-90329 proposes a capacitance humidity sensor. However, the relative humidity changes with temperature even for the same water content. Japanese Patent Laid-Open No. 6-242048 proposes a heat conduction type humidity sensor which performs compensation by temperature. Also, Japanese Patent Laid-Open No. 5-149901 proposes a humidity sensor obtained by forming two temperature-sensitive elements in parallel on the same substrate.

In temperature and humidity measurements, necessary specifications depend on applications. For example, in houses and offices, to keep comfortable living environments by finely controlling the operating conditions of, e.g., air-conditioners, the humidity and temperature distributions in living spaces must be measured. Food processors such as microwave ovens require a small-sized environment sensor capable of high-speed response in order to efficiently perform a variety of cooking. Furthermore, to perform optimal image formation in business machines such as copying machines, measurements of the temperature and humidity of printing sheets which change from moment to moment must be performed at higher speed in more detail than when performed by the conventional sensors. Also, in the fabrication processes of various IC circuits and the like, the environmental factors such as the temperature and humidity are required to be measured at higher accuracy than those of the conventional sensors.

Conventionally, the temperature and humidity are separately measured by a temperature measurement sensor and humidity measurement sensor. This increases the environment sensor scale, and prevents downsizing of sensors. In addition, the response speed is low in humidity measurement. Accordingly, the conventional humidity sensor cannot be used to set printing conditions when high-speed printing is to be performed by a copying machine or the like.

Also, with the spread of the Internet, information in a remote place is often processed by a server. This increases the necessity to transmit signals from environment sensors by radio.

SUMMARY OF THE INVENTION

Accordingly, the present invention provides an environment sensor for measuring the temperature and humidity, which can be miniaturized and can respond at high speed.

According to the present invention, the foregoing issue is solved by an environment sensor comprising a temperature sensor containing a temperature-sensitive material made of a metal oxide, and a humidity sensor which measures an ambient humidity by using a change in electrical characteristic, wherein at least one of a pair of electrodes of the temperature sensor is integrated with an electrode of the humidity sensor.

The invention is particularly advantageous since the environment sensor for measuring the temperature and humidity can be miniaturized and can respond at high speed. It is possible by using this environment sensor to provide an environment measurement apparatus and environment measurement system which realize high-speed measurements.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 4 is a graph showing the relative humidity measured by the environment sensor according to the first embodiment and the conventional humidity sensor;

FIG. 10 is a conceptual view showing an environment measurement system according to the fourth embodiment of the present invention.

DETAILED DESCRIPTION OF THE PREFERRED EMBODIMENTS

Figure 1A:
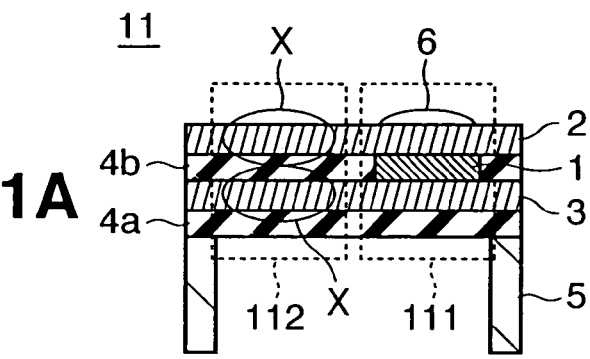
FIG. 1A is a schematic sectional view of an environment sensor according to an embodiment.

Preferred embodiments of the present invention will now be described in detail in accordance with the accompanying drawings.

Numerical values used in the following explanation are merely examples unless otherwise specified. Accordingly, these numerical values do not limit the present invention.

The present invention provides an environment sensor for measuring the temperature and humidity, which can be miniaturized and can respond at high speed. In the present invention, the miniaturization and high-speed response are realized as follows. That is, the miniaturization is realized by forming a temperature sensing portion (temperature sensor) and humidity sensing portion (humidity sensor) on the same substrate, and measuring the humidity by using the same electrode as the temperature sensor. The high-speed response is realized by using a hollow structure as the structure of the environment sensor.

More specifically, to realize high-speed response, it is necessary to decrease the heat capacities of a temperature sensing portion and humidity sensing portion by miniaturizing these sensing portions, and simplifying the arrangements of these sensing portions. In the first embodiment of the environment sensor of the present invention, therefore, a temperature sensor in which a temperature-sensitive material is a metal oxide and a humidity sensor which uses changes in electrical characteristics are integrated. In addition, at least one of a pair of electrodes of the temperature sensor is integrated with an electrode of the humidity sensor. In the second embodiment of the environment sensor of the present invention, a pair of stacked bodies having a multi-layered structure of lower electrode/metal oxide layer/upper electrode are formed on the same substrate. One stacked body is used as a temperature sensor, and the other stacked body is used as a humidity sensor. The pair of stacked bodies share the electrodes.

A ferroelectric or pyroelectric is used as the material of the metal oxide layer of the temperature sensor. When the ambient temperature of the metal oxide layer changes, electric charge is generated on the surface of the metal oxide layer in accordance with the change amount. The temperature is measured by measuring a voltage corresponding to the generated electric charge. In addition, the heat radiation efficiency is increased by reducing the heat capacities of the temperature sensing portion and humidity sensing portion by using the environment sensor hollow structure, i.e., by removing the substrate from the temperature and humidity sensing portions. This makes high-speed response feasible.

Also, an environment measurement apparatus for measuring the temperature and humidity by using the environment sensor described above comprises a signal detecting unit for measuring the electrical properties of and between electrodes of each sensor, a signal processing unit which processes a signal from the signal detecting unit into a desired form and calculates measurement results, and a transmitting/receiving unit which transmits a signal from the signal processing unit to an external apparatus. Examples of the electrical properties measured by the signal detecting units are the electrical resistance of the electrode, the electric power input to hold the environment sensor at a predetermined temperature, and the electric current amount. The humidity can be measured on the basis of these measurements. Also, the temperature can be measured by measuring the voltage between the electrodes. In these measurements, the relative humidity, absolute water content, temperature, and the like are calculated by processing the output from the signal detecting unit by using the signal processing unit. The transmitting/receiving unit transmits the result signal to an external apparatus such as a display or personal computer. This signal transmission is performed by various types of radio in order to reduce the limitations on locations of environmental measurements.

(First Embodiment)

Figure 1B:
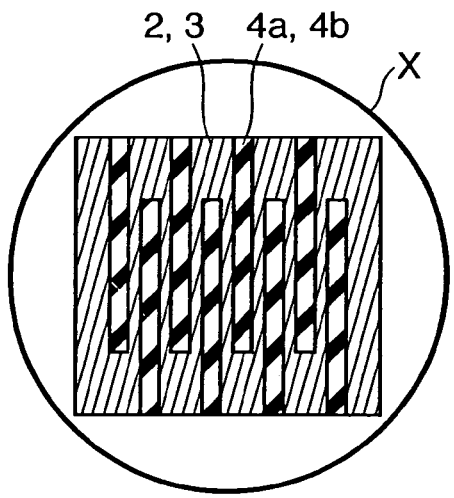
FIG. 1B is a schematic enlarged plan view of electrodes in a humidity sensing region of the environment sensor according to the embodiment.
Figure 1C:
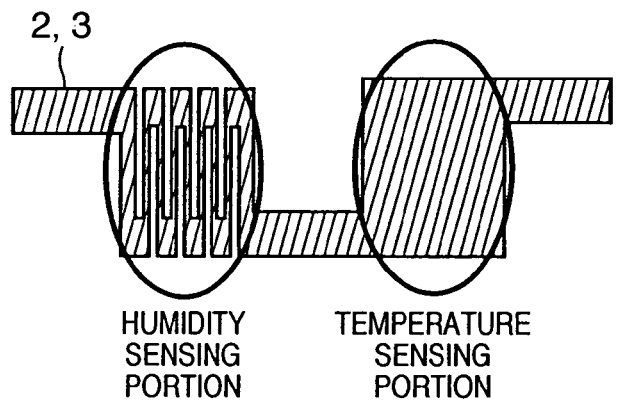
FIG. 1C is a schematic plan view of the electrodes of the environment sensor shown in FIG. 1A.
Figure 1D:
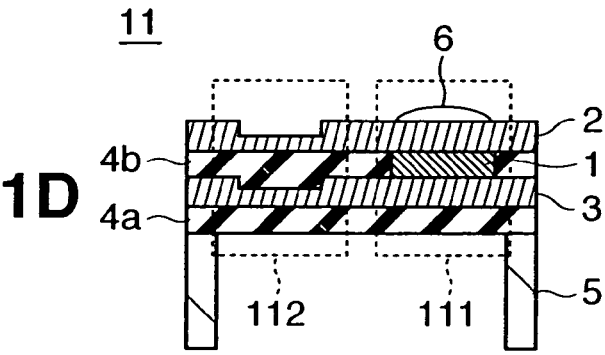
FIG. 1D is a schematic sectional view of another environment sensor according to the first embodiment.

FIGS. 1A to 1D illustrate an outline of the arrangement of an environment sensor according to the first embodiment of the present invention. FIG. 1A is a schematic sectional view of the environment sensor. FIG. 1B is a schematic enlarged plan view of electrodes in a humidity sensing region X of the environment sensor. Note that FIG. 1B is not a view obtained by directly enlarging the section of the circle X in FIG. 1A, but a view obtained by enlarging a plan view of the circle X. FIG. 1C is a schematic plan view of electrodes of the environment sensor shown in FIG. 1A. FIG. 1D is a schematic sectional view of another environment sensor according to the first embodiment. Although FIGS. 1A to 1D illustrate only portions of the sensor, the overall shape of the sensor is a substantially rectangular shape. Since this shape is, of course, merely an example, the present invention is not limited to this shape.

An environment sensor 11 according to this embodiment includes a temperature sensing portion 111 and humidity sensing portion 112. Reference numeral 1 denotes a metal oxide layer; 2, an upper electrode; 3, a lower electrode; 4a and 4b, insulator layers; 5, a substrate; and 6, an infrared transmitting material.

The temperature sensing portion 111 has a three-layered structure including the upper electrode 2, metal oxide layer 1, and lower electrode 3. As the material of the metal oxide layer 1, a ferroelectric, pyroelectric, or the like is used.

The temperature measurement principle is as follows. When infrared radiation transmitted through the infrared transmitting material 6 enters the metal oxide, electric charge is generated by the pyroelectric characteristics of the metal oxide. The thus generated electric charge is measured as a voltage between the electrodes, and the temperature is obtained on the basis of the measured voltage. Since near the Curie point the dielectric constant largely changes in accordance with the temperature, it is, of course, also possible to use this change in dielectric constant. When the temperature is to be measured on the basis of this dielectric constant change, the change in dielectric constant is obtained by measuring the electrical capacitance or electrical resistance between the electrodes, and the temperature is obtained from this dielectric constant change.

As shown in FIG. 1A, the humidity sensing portion 112 has the lower electrode 3 and upper electrode 2 with the insulator layer 4b interposed between them. The upper electrode 2 and lower electrode 3 are formed into a shape as shown in the plan views of FIGS. 1B and 1C. The thus formed humidity sensing portion is exposed to the measurement ambient directly or indirectly via a filter or the like, and the humidity is measured using the electrical characteristics between the electrodes. Examples of the electrical characteristics of the electrodes are the electrical resistance, and the amount of electric current flowing through the electrodes.

The filter is used to remove substances, e.g., dust, other than water, in the ambient. This filter is not an essential element. If a substance, e.g., strongly acidic steam, other than dust is present in the ambient, the sensor portions are protected by a porous material which readily adsorbs or absorbs the substance. This prolongs the sensor life. When the filter is used, the flow of air is more or less limited. Therefore, the measurement speed slightly decreases compared to that when no such filter is used. This decrease in measurement speed depends on the material of the filter. Generally, the larger the pores of the porous material, the smaller the decrease; the smaller the pores, the larger the decrease. Whether to use a filter and how to select the material of the filter are appropriately determined in accordance with the application of the sensor.

The shape of the upper and lower electrodes 2 and 3 in the humidity sensing portion 112 is not limited to the shape as shown in FIGS. 1B and 1C, but can also be a spiral shape or the like. The humidity sensing portion 112 senses the water content from a change in electrical resistance when the electrode portion adsorbs water. Accordingly, the surface area of the humidity sensing portion 112 is preferably as large as possible because a large amount of water can be adsorbed. That is, the sensitivity, the S/N of a sensing signal, and the like are determined in accordance with the surface area of the humidity sensing portion 112. Therefore, a linear electrode is disadvantageous because the resistance change is small. On the other hand, a zigzagged structure (FIG. 1B) or spiral structure is advantageous because the electrode length can be increased. Alternatively, as shown in FIG. 1D, the film thickness of that portion of the humidity sensing portion 112, which adsorbs water can be made smaller than the film thickness of the electrode portion of the temperature sensing portion 111. The line width of the water adsorbing portion of the humidity sensing portion 111 may also be decreased.

More specifically, the electrode portion of the humidity sensing portion 112 need only have a structure having an electrical resistance larger than that of the peripheral electrode portion. When the water adsorbing portion and the other portion (which does not adsorb water) have the same length, the electrical resistance of the water adsorbing portion is normally set to be 2 to 100 times that of the other portion.

The plan view of the electrode portion shown in FIG. 1C shows the square temperature sensing portion 111. However, the present invention is not limited to this shape.

An example of a method of manufacturing the environment sensor shown in FIG. 1D will be explained below. FIGS. 2A to 2J illustrate the manufacturing steps of the environment sensor shown in FIG. 1D.

Figure 2A:
FIGS. 2A to 2J are sectional views showing the manufacturing steps of the environment sensor shown in FIG. 1D.

First, as shown in FIG. 2A, an insulator layer 4a is formed on a silicon substrate 5. The insulator layer 4a is made of, e.g., silicon dioxide, and formed to have a film thickness of about 2 μm by RF sputtering.

Figure 2B:
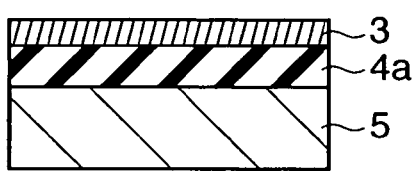

Subsequently, as shown in FIG. 2B, a lower electrode 3 made of platinum/titanium is formed on the insulator layer 4a by RF sputtering. More specifically, after titanium is deposited by about 50 nm, platinum is deposited by about 600 nm to form the lower electrode 3. Although the thicknesses of titanium and platinum may also be about 50 to 100 nm and 500 to 1,000 nm, respectively, it is, of course, also possible to use other values.

Figure 2C:
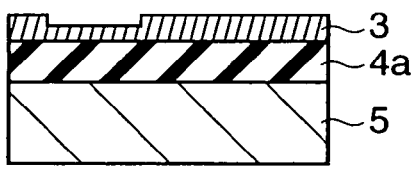

As shown in FIG. 2C, a resist pattern (not shown) for forming a humidity sensor formation region is formed by photolithography. After that, the thickness of the lower electrode 3 in this humidity sensor formation region is made smaller than that in the surrounding portion by dry etching. In this state, the humidity sensor formation region is formed in a position about 200 μm from a temperature sensor formation region. Referring to FIG. 1C, 200 μm is the distance between the edges of the temperature sensing portion and humidity sensing portion, and equal to the length of the electrode (the central portion shown in FIG. 1C) connecting these edges. In this humidity sensor formation region, the lower electrode 3 has a film thickness of about 150 nm and a width of about 30 μm.

After that, the resist pattern (not shown) is removed by ashing or the like. The planar shape of the lower electrode 3 in this humidity sensor formation region formed by etching is not limited, i.e., can be any shape such as a square, circle, or ellipse.

Figure 2D:
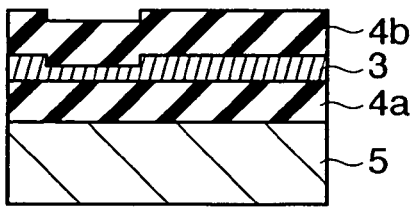

As shown in FIG. 2D, silicon dioxide is deposited by about 3 μm by RF sputtering to form an insulator layer 4b.

Figure 2E:
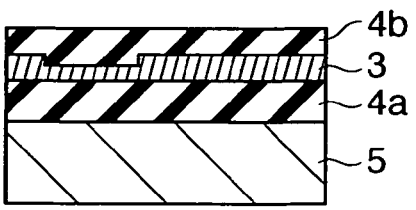

As shown in FIG. 2E, the surface of the insulator layer 4b is planarized by, e.g., drying etching or polishing. In this embodiment, the following steps may also be performed, without any planarization, while the surface of the insulator layer 4b is kept lower than that of the surrounding portion.

Figure 2F:
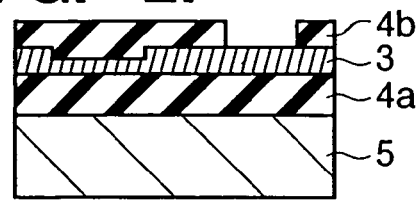

As shown in FIG. 2F, a resist pattern (not shown) for forming a temperature sensor formation region is formed by photolithography. After that, dry etching is performed using a solution mixture of hydrofluoric acid and nitric acid, thereby removing the insulator layer 4b from the temperature sensor formation region.

Figure 2G:
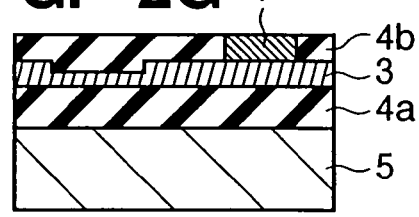

As shown in FIG. 2G, (Pb, La)(Zr, Ti)O$_3$ (Pb/La=95/5, Zr/Ti=35/65 atomic ratio or less, to be referred to as PLZT hereinafter) is deposited to have a film thickness of about 3 μm by MOCVD. In addition, the resist pattern (not shown) is removed by a lift-off method to form a metal oxide layer 1 made of PLZT only in the temperature sensor formation region. The metal oxide layer 1 is a square layer of about 500 μm side.

Figure 2H:
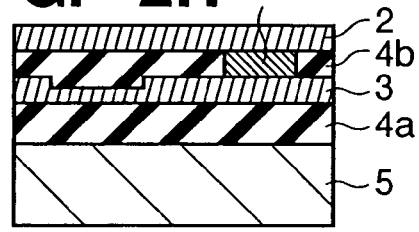
Figure 2I:
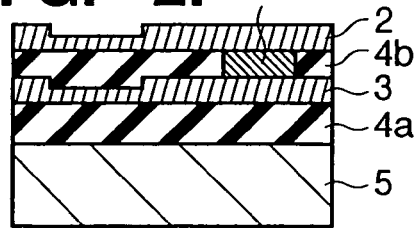

As shown in FIG. 2H, an upper electrode 2 made of platinum/titanium is formed to have a film thickness of about 1 μm by RF sputtering. Subsequently, as shown in FIG. 2I, a resist pattern (not shown) for forming a humidity sensor formation region is formed by photolithography. After that, the thickness of the upper electrode 2 in this humidity sensor formation region is made smaller than that in the surrounding portion by dry etching. The resist pattern (not shown) is then removed by ashing or the like.

Figure 2J:
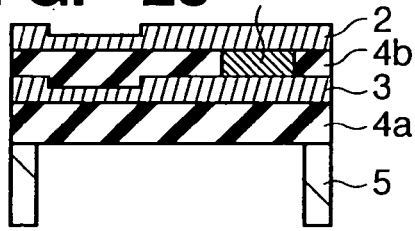

As shown in FIG. 2J, the substrate 1 in the temperature sensor formation region and humidity sensor formation region is removed by etching. An environment sensor 11 thus obtained is then placed in a stainless steel pipe having an inside diameter of 3 mm and an outside diameter of 3.5 mm, and fixed by an epoxy resin. In this manner, the environment sensor according to this embodiment is completed.

In this environment sensor, an optical system such as the infrared transmitting member 6 shown in FIG. 1A or 1D which is used to efficiently collect infrared radiation and control the measurement viewing angle may also be formed on the upper electrode 2 in the temperature sensor formation region. It is also possible to form an infrared reflecting film made of, e.g., gold on the upper electrode 2 in the humidity sensor formation region to remove the effect of the temperature. The size, the types of constituent materials, the film thickness, the film formation method, and the patterning method of each of these sensors can be freely selected in accordance with the purpose.

In this embodiment, the metal oxide layer 1 can be made of any material as long as the material is a ferroelectric or pyroelectric, and preferably has a perovskite structure. Practical examples are Pb—La—Zr—Ti—O, Bi—Ti—O, Ba—Sr—Ti—O, Li—Ta—O, Li—Nb—O, and their mixtures. Although various types of materials having a pyroelectric effect exist, a perovskite structure has a relatively large pyroelectric effect. The use of a material having a large pyroelectric effect is more advantageous than the use of a material having a small pyroelectric effect, since a highly reliable sensor can be manufactured.

To measure the temperature and humidity with extremely high accuracy, the substrate 1 of the environment sensor need only be installed in a space in which the temperature and humidity are controlled. Since in this case the lower electrode 3 is always held under predetermined environmental conditions, it is possible to sense not only the electrical characteristics of the upper electrode 2 but also the difference between the electrical characteristics of the upper and lower electrodes 2 and 3.

Figure 3:
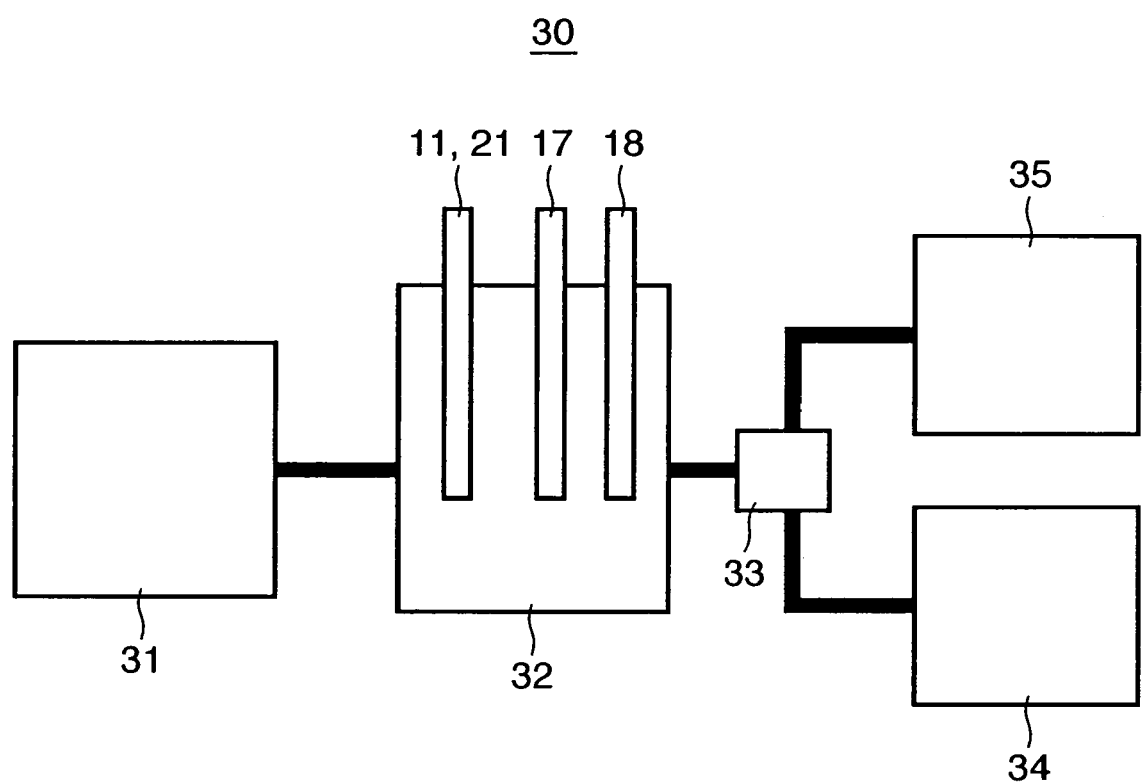
FIG. 3 is a schematic view showing the arrangement of a laboratory device for evaluating the characteristics of the environment sensor.

A laboratory device having an arrangement shown in FIG. 3 was used to evaluate the characteristics of the environment sensor 11 shown in FIG. 1D.

FIG. 3 is a schematic view showing the arrangement of the laboratory device for evaluating the characteristics of the environment sensor. In a laboratory device 30 shown in FIG. 3, reference numeral 32 denotes a cylindrical sample vessel in which the environment sensor 11 according to this embodiment, a conventional temperature sensor 17, and a conventional humidity sensor 18 are spaced at an angle of 120°. The total volume of the sample vessel 32 is 100 ml. In this experiment, a mercury thermometer (outside diameter 7 mm) was used as the conventional temperature sensor 17, and the HS-05 sensor manufactured by HOKURIKU ELECTRIC INDUSTRY (a sensor portion has a width of 7 mm, a length of 10.5 mm, and a height of 4 mm) was used as the humidity sensor 18.

Each of a high-humidity vessel 34 and low-humidity vessel 35 was filled with air held at a predetermined temperature and predetermined relative humidity. The temperature and humidity of each vessel were measured with the conventional temperature sensor 17 and conventional humidity sensor 18, respectively. A suction apparatus 31 supplies air having a saturated vapor pressure in the high-humidity vessel 34 or low-pressure vessel 35 to the sample vessel 32 via a flow path switching device 33.

In this characteristic evaluation experiment, the low-humidity vessel 35 and high-humidity vessel 34 were previously filled with air having a relative humidity of 15% RH and air having a relative humidity of 90% RH, respectively, at atmospheric pressure at a temperature of 25° C. In this state, the air in the low-humidity vessel 35 was drawn by suction into the sample vessel 32, and the temperature and humidity were measured by the environment sensor 11, conventional temperature sensor 17, and conventional humidity sensor 18.

Subsequently, the flow path switching device 33 was switched to replace the air in the sample vessel 32 with the air from the high-humidity vessel 34. By setting this flow path switching time as an origin, the internal temperature and humidity of the sample vessel 32 were measured by the environment sensor 11, conventional temperature sensor 17, and conventional humidity sensor 18. The measurement interval of the environment sensor 11 was 30 ms, and that of the conventional temperature sensor 17 and conventional humidity sensor 18 was 1 to 20 s.

FIG. 4 is a graph showing the relative humidity measured by the environment sensor of this embodiment and the conventional humidity sensor.

The environment sensor 11 according to this embodiment measured a relative humidity change amount of about 80% in 30 ms, and a change of about 90% in 50 ms. On the other hand, the conventional humidity sensor 18 required a time of about 3.5 min before a relative humidity change amount of about 90% was measured.

When 6 minutes elapsed after that, the air in the sample vessel 32 was switched to the air from the low-humidity vessel 35 again. In this state, the environment sensor 11 according to this embodiment measured a change of about 80% in 30 ms, and the same humidity as in the low-humidity vessel 35 in 60 ms. By contrast, the conventional humidity sensor 18 measured only a change of about 20% even after an elapse of 1 min.

Also, during this relative humidity change measurement, the conventional temperature sensor 17 measured no change in internal temperature of the sample vessel 32. On the other hand, the environment sensor 11 according to this embodiment measured a temperature drop of 0.2° C. to 0.4° C. from 25° C. immediately after the flow paths were switched, and measured a temperature of 25° C.±0.1° C. after that. This temperature change immediately after the flow paths were switched was presumably caused by a pressure change in the sample vessel 32 since the switch of the suction apparatus 31 operated earlier by about 0.3 s than the flow path switching device 33.

As described above, the environment sensor 11 according to this embodiment had sensing portions smaller than those of the conventional temperature sensor 17 and conventional humidity sensor 18, and was capable of high-speed measurement, i.e., capable of measuring a change of 90% RH for 1 s or less.

(Second Embodiment)

Figure 5A:
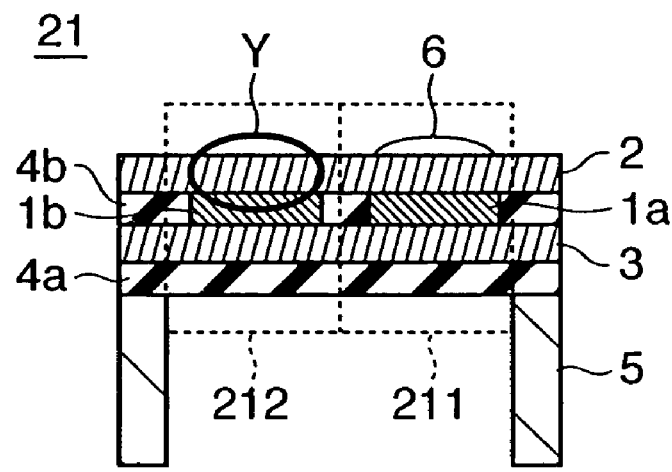
FIG. 5A is a schematic sectional view of an environment sensor according to the second embodiment.
Figure 5B:
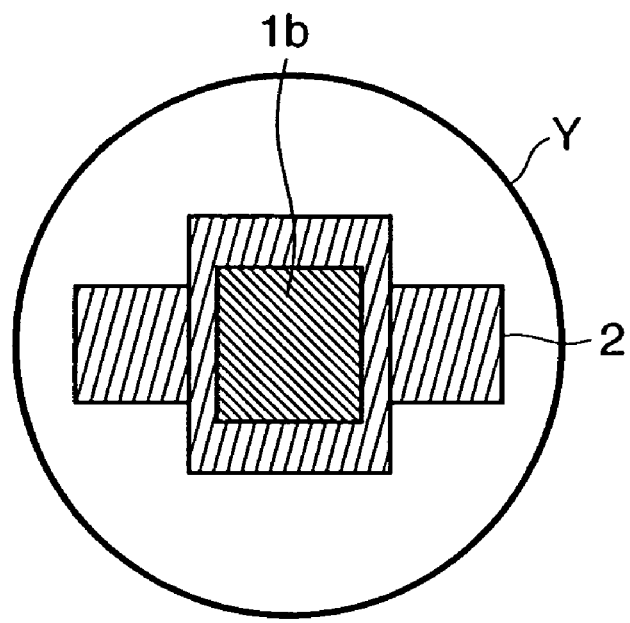
FIG. 5B is a schematic enlarged plan view of electrodes in a humidity sensing region of the environment sensor shown in FIG. 5A.

FIGS. 5A and 5B illustrate an outline of the arrangement of an environment sensor according to the second embodiment of the present invention. FIG. 5A is a schematic sectional view of the environment sensor. FIG. 5B is an enlarged plan view of electrodes in a humidity sensing region of the environment sensor shown in FIG. 5A. That is, the sensor is viewed from the side in FIG. 5A, and viewed from the above in FIG. 5B.

As shown in FIG. 5A, an environment sensor 21 according to this embodiment includes a temperature sensing portion 211 and humidity sensing portion 212. Reference numerals 1a and 1b denote metal oxide layers; 2, an upper electrode; 3, a lower electrode; 4a and 4b, insulator layers; 5, a substrate; and 6, an infrared transmitting material. The metal oxide layers 1a and 1b are made of a ferroelectric or pyroelectric. Although the infrared transmitting material 6 is so formed as to have a curved surface in FIG. 5A, the shape is not particularly limited. The infrared transmitting material 6 need only be formed if necessary.

As shown in FIG. 5A, the temperature sensor 211 and humidity sensor 212 have a pair of stacked bodies having a three-layered structure including the lower electrode 3, the metal oxide layers 1a and 1b formed on the lower electrode 3, and the upper electrode 2 formed on the metal oxide layers 1a and 1b. Also, the lower electrode of the temperature sensor 211 and the lower electrode of the humidity sensor 212 are connected. Likewise, the upper electrodes are also connected.

As shown in FIG. 5B which is an enlarged plan view of the upper electrode 2 of the humidity sensor 212, the upper electrode 2 is so formed as to expose a portion of the metal oxide layer 1b. The electrode shape of this exposed portion is not limited to a square, but can be a circle, spiral, or zigzag. Also, the exposed area of the metal oxide layer 1b can be freely determined in accordance with the application.

For example, to measure a humidity change at high speed, a standard is about 50% or more.

The metal oxide layer 1b in this embodiment is preferably polycrystalline, rather than single-crystal. That is, humidity measurement in this embodiment uses a change in capacitance or electrical resistance between the electrodes, which is caused by water adsorbed by the metal oxide layer 1b. When the metal oxide layer 1b is single-crystal, therefore, only adsorbed water on the surface is used. However, when the metal oxide layer 1b is polycrystalline, the surface area increases, and water diffused and adsorbed in crystal grain boundaries can also be used. Accordingly, when the metal oxide layer 1b is polycrystalline, the electrical capacitance between the electrodes can be measured over a broader range and the electrical resistance changes more rapidly than when the metal oxide layer 1b is single-crystal.

Temperature measurement is performed by using a pyroelectric effect by which electric charge is generated on the surface of the metal oxide layer 1a when heat is conducted to it, or by using the phenomenon in which the dependence of the dielectric constant on the temperature is large near the Curie temperature. The crystallinity of the metal oxide layer 1a is not limited, so the metal oxide layer 1a can be either single-crystal or polycrystalline. In order to simplify the manufacturing steps, the metal oxide layers 1a and 1b are desirably made of the same material and given the same crystal state. However, it is also possible to use different materials or give different crystal states in accordance with the application.

An example of a method of manufacturing the environment sensor 21 shown in FIGS. 5A and 5B will be explained below.

FIGS. 6A to 6H illustrate the manufacturing method of the environment sensor shown in FIGS. 5A and 5B in order of steps.

Figure 6A:
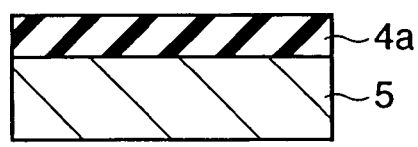
FIGS. 6A to 6H are views showing the manufacturing steps of the environment sensor shown in FIG. 5A.

First, as shown in FIG. 6A, an insulator layer 4a is formed on a silicon substrate 5. The insulator layer 4a is made of, e.g., silicon dioxide, and formed to have a film thickness of about 1 μm by RF sputtering.

Figure 6E:
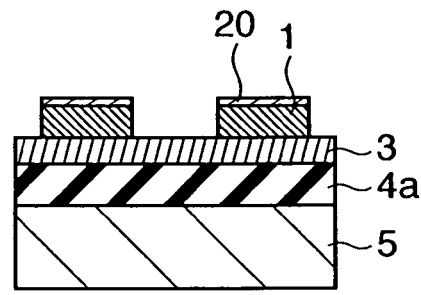
Figure 6B:
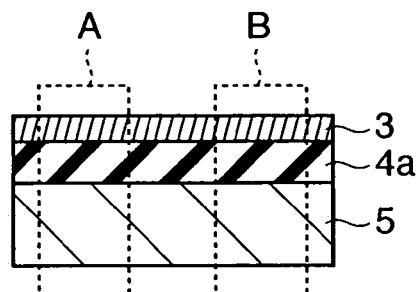

Subsequently, as shown in FIG. 6B, a gold paste coating about 15 μm thick is formed by screen printing. After that, the gold layers in a temperature sensor formation region and humidity sensor formation region undergo respective predetermined processes to form a lower electrode 3.

More specifically, a temperature sensor formation region is formed as a square region of about 350 μm side. A humidity sensor formation region is formed as a square region of about 300 μm, and a square hole of about 160 μm side is formed inside this humidity sensor formation region. These temperature sensor formation region and humidity sensor formation region are spaced by about 200 μm, and the width of the lower electrode 3 in a portion connecting them is about 100 μm. Reference symbols A and B shown in FIG. 6B denote the humidity sensor formation region and temperature sensor formation region, respectively.

Figure 6F:
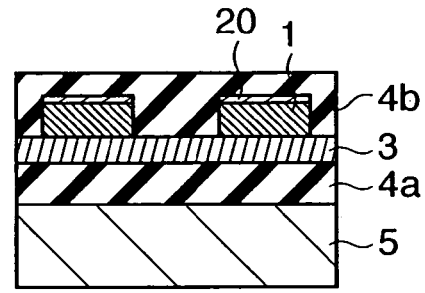
Figure 6C:
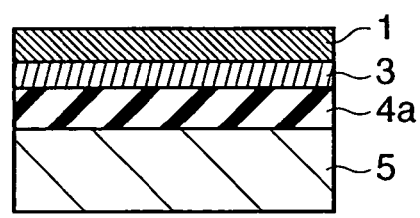
Figure 6G:
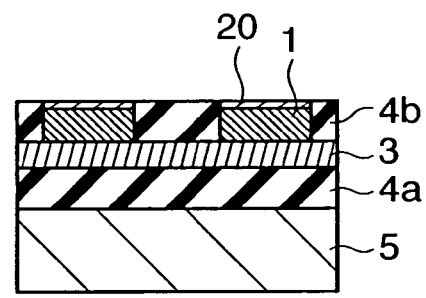
Figure 6D:
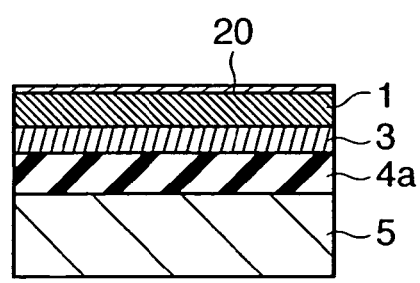

As shown in FIG. 6C, a metal oxide layer 1 made of $Bi_4Ti_3O_{12}$ (to be referred to as BIT hereinafter) is formed to have a film thickness of about 30 μm by screen printing. Subsequently, as shown in FIG. 6D, a titanium layer 20 about 100 nm thick is formed by RF sputtering.

As shown in FIG. 6E, a resist pattern covering the temperature sensor formation region and humidity sensor formation region are formed by photolithography. Dry etching is then performed to leave the titanium layer 20 only in the temperature sensor formation region and humidity sensor formation region. In addition, wet etching using a solution mixture of hydrofluoric acid and nitric acid is performed to form a metal oxide layer 1a in the temperature sensor formation region and a metal oxide layer 1b in the humidity sensor formation region.

As shown in FIG. 6F, an insulator layer 4b made of silicon dioxide is formed by ion beam sputtering. Subsequently, as shown in FIG. 6G, the insulator layer 4b is planarized by etching to an interface to which the titanium layer 20 is exposed.

Figure 6H:
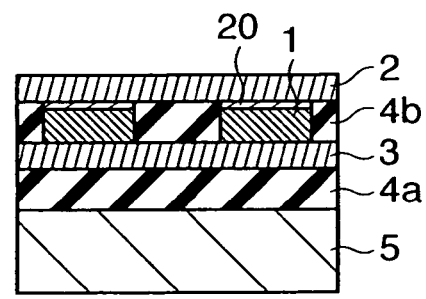

As shown in FIG. 6H, a titanium layer and platinum layer are continuously formed by RF sputtering. These platinum and titanium layers are then patterned by photolithography such that an electrode in each of the temperature sensor formation region and humidity sensor formation region has the same size as or a size smaller by about 10 μm than that of the lower electrode 3, thereby forming an upper electrode 2. After that, an environment sensor 21 thus obtained is placed in a stainless steel pipe having an inside diameter of 4 mm and an outside diameter of 5 mm, and fixed by an epoxy resin. In this manner, the environment sensor according to this embodiment is completed. In this environment sensor, an optical system such as the infrared transmitting member 6 shown in FIG. 5A which is used to efficiently collect infrared radiation and control the measurement viewing angle may also be formed on the upper electrode 2 in the temperature sensor formation region. It is also possible to form an infrared reflecting film made of, e.g., gold on the upper electrode 2 in the humidity sensor formation region to remove the effect of the temperature.

Following the same procedures as in the first embodiment, a laboratory device having an arrangement shown in FIG. 3 was used to evaluate the characteristics of the environment sensor 21 shown in FIGS. 5A and 5B. The evaluation method was also the same as in the first embodiment, i.e., the method was comparison with the conventional sensors.

First, referring to FIG. 3, the environment sensor 21 was set in place of the environment sensor 11 of the first embodiment. The characteristic measurement method was as follows. First, the same environment as in a low-humidity vessel 35 was formed in a sample vessel 32, and this ambient in the sample vessel 32 was then switched to the environment in a high-humidity vessel 34 by a flow path switching device 33. When 20 milliseconds elapsed after the flow path switching device 33 was operated, measurements by the environment sensor 21, a conventional temperature sensor 17, and a conventional humidity sensor 18 were started. Note that the interior of the low-humidity vessel 35 was controlled to a temperature of 20° C. and a humidity of 5% RH, and the interior of the high-humidity vessel 34 was controlled to a temperature of 20° C. and a relative humidity of 85% RH. Note also that in this experiment, a mercury thermometer was used as the conventional temperature sensor 17, and the HS-05 sensor manufactured by HOKURIKU ELECTRIC INDUSTRY was used as the conventional humidity sensor 18.

The temperature measurement results of the environment sensor 21 and conventional temperature sensor 17 were substantially the same.

Figure 7:
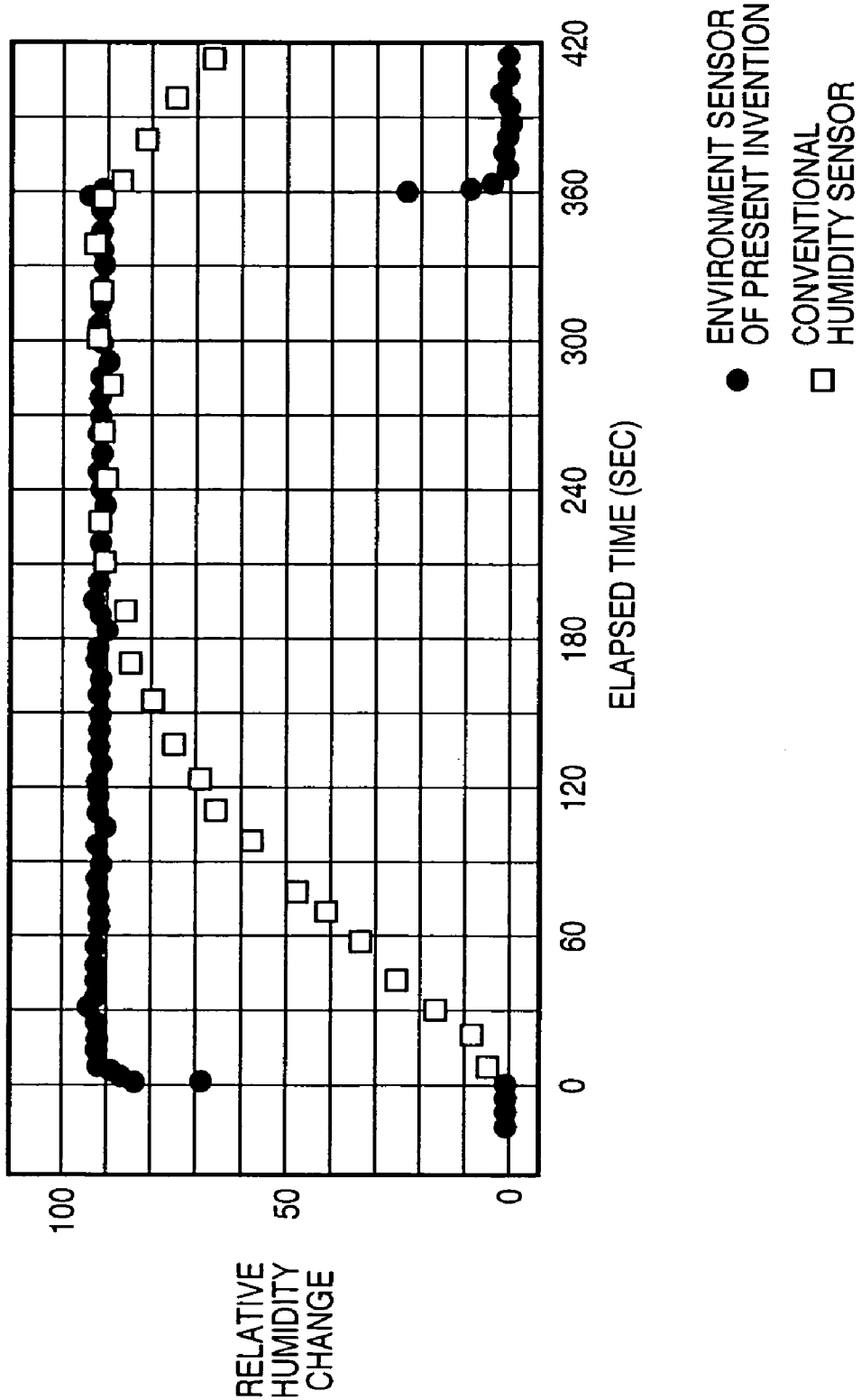
FIG. 7 is a graph showing the relative humidity measured by the environment sensor according to the second embodiment and the conventional humidity sensor.

The humidity measurement results are shown in FIG. 7. FIG. 7 is a graph showing the relative humidity measured by using the environment sensor according to this embodiment and the conventional humidity sensor.

As shown in FIG. 7, the relative humidity change amounts measured by the environment sensor 21 according to this embodiment were about 70% in 50 ms, about 80% in 100 ms, and about 90% in 4 s. On the other hand, the conventional humidity sensor 18 required a time of about 3.5 min before a relative humidity change amount of about 90% was measured.

As described above, similar to the environment sensor 11 of the first embodiment, the environment sensor 21 of this embodiment also had a higher response speed than that of the conventional sensor.

(Third Embodiment)

The third embodiment of the present invention relates to an environment measurement apparatus including the environment sensor according to the present invention.

Figure 8:
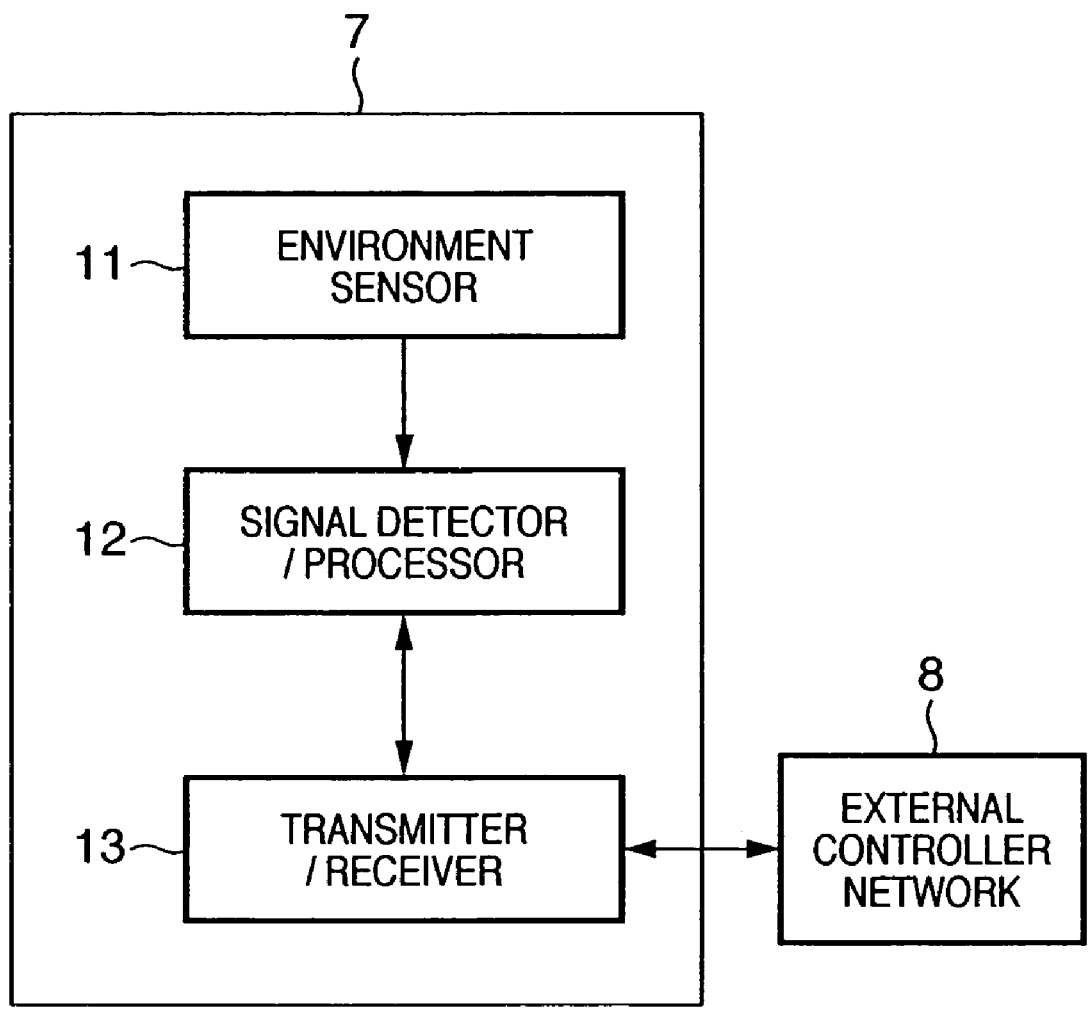
FIG. 8 is a block diagram of an environment measurement apparatus according to the third embodiment of the present invention.

FIG. 8 is a block diagram showing the environment measurement apparatus according to the third embodiment of the present invention.

An environment measurement apparatus 7 includes an environment sensor 11 according to the present invention which measures the temperature and humidity, a signal detector/processor 12 which detects and processes an output electrical signal from the environment sensor 11, and a transmitter/receiver 13 having functions of transmitting a signal from the signal detector/processor 12 to an external controller 8, and transmitting instructions from the external controller 8 to the signal detector/processor 12.

The signal detector/processor 12 measures the electrical resistances and electric currents of the electrodes, and the capacitance, resistance, and voltage between the electrodes of the environment sensor 11. The signal detector/processor 12 can have any circuit configuration as long as these electrical characteristics can be detected and processed. The transmitting/receiving method of the transmitter/receiver 13 is radio communication at an arbitrary frequency, e.g., optical communication, microwave communication, or millimeter wave communication. A preferable frequency and preferable communicating means can be selected in accordance with the application.

It is, of course, also possible to use a controller such as a microprocessor and a memory, if necessary, in addition to the signal detector/processor 12 and transmitter/receiver 13. Although not shown in FIG. 8, the environment measurement apparatus 7 can also incorporate a power supply such as a secondary battery, fuel cell, or solar cell, or means for externally supplying electric power by microwave irradiation. Furthermore, the environment measurement apparatus 7 can also have means, e.g., a GPS, for specifying the location of the apparatus itself.

The results of temperature and humidity measurements performed by using the environment measurement apparatus 7 according to this embodiment will be described below.

Figure 9:
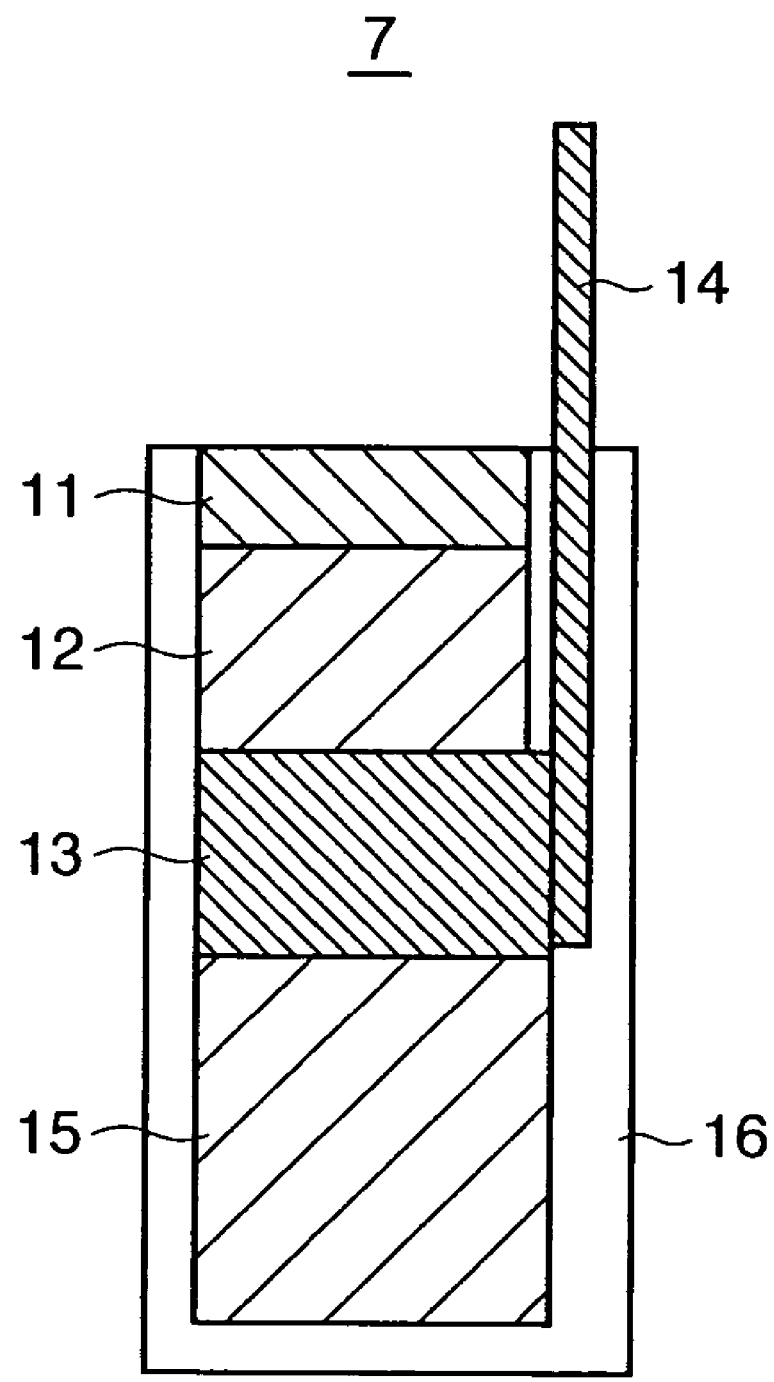
FIG. 9 is a schematic view showing the arrangement of the environment measurement apparatus shown in FIG. 8.

FIG. 9 is a schematic view showing the arrangement of the environment measurement apparatus 7 shown in FIG. 8.

The environment measurement apparatus 7 comprises the environment sensor 11, the signal detector/processor 12, the transmitter/receiver 13, an antenna 14 for communicating with an external controller, a power supply 15, and a container 16 which contains these members. A lithium ion secondary battery was used as the power supply 15 so that the environment measurement apparatus 7 was usable even in a place where external power supply was difficult.

The practical structure of the environment sensor 11 can be the typical structure shown in FIG. 1 or 2. In this embodiment, the environment sensor shown in FIG. 1 is used. Also, a metal oxide layer 1 of the environment sensor was formed by using (Ba, Sr)TiO$_3$ as a material. The surface of a temperature sensing portion 111 was a circle having a diameter of 5 mm, and an electrode in a humidity sensing portion 112 had a total length of 1 mm, a width of 200 µm, and a film thickness of 10 µm. The electrode width in the other portion was 500 µm. The spacing between the temperature sensing portion 111 and the humidity sensing portion 112 was 2 mm.

The signal detector/processor 12 can be any device, provided that the device can detect the electric current flowing through an upper electrode 2 and lower electrode 3 of the environment sensor and can detect the voltage and resistance between these electrodes. Also, the transmitter/receiver 13 is not limited as long as radio connection to the external controller is possible. In this embodiment, a radio wave of 348 to 349 MHz was used. For this purpose, a pole antenna was used as the antenna 14 to be able to exchange signals at a distance of a maximum of about 10 m. The constituent elements denoted by reference numerals 11 to 15 were accommodated in the aluminum container 16. The container 16 was a cylindrical container having an outside diameter of 10 cm and a height of 15 cm. The container 16 was filled with air having an absolute water content of 20 g/m$^3$.

The environment measurement apparatus 7 described above was used to continuously measure the temperature and humidity over 8 hrs in a position 50 cm eastward from an instrument shelter for weather observation at 1 m above the ground in the open air. The measurement method was such that the measurement start time, measurement end time, measurement intervals, and the like were transmitted on signals from a personal computer inside a house to the transmitter/receiver 13 of the environment measurement apparatus, and the measurement results were loaded into the personal computer every 30 min. As a consequence, the differences between the measurements by the instrument shelter and the environment measurement apparatus 7 of this embodiment were only a temperature of ±1° C. and a humidity of ±3% RH.

(Fourth Embodiment)

The fourth embodiment of the present invention relates to an environment measurement system which measures the temperature and humidity by using the environment measurement apparatus according to the present invention.

FIG. 10 is a conceptual view showing the environment measurement system according to the fourth embodiment of the present invention.

In this embodiment, measurements of the temperature and humidity distributions performed in a space 10 having an arbitrary volume when air having a controlled temperature and humidity is supplied to the space 10 from an air blower 9 such as an air-conditioner will be explained.

Referring to FIG. 10, the air blower 9 comprises a heater, cooler, water container, fan, flow rate controller, and the like. An air stream blown from the air blower 9 is supplied between arrows indicated by X in FIG. 10. The direction and divergence angle of this air stream can be freely controlled. The space 10 is a rectangle 5 m in length, 9 m in width, and 5 m in height.

Environment measurement apparatuses 7 were arranged at random on the floor of the space 10. However, environment measurement apparatuses A to G shown in FIG. 10 were arranged such that the environment measurement apparatus A was positioned perpendicularly to the air blower 9 at a distance of 1 m, and the environment measurement apparatuses B to G were arranged at an interval of 1 m. The other environment measurement apparatuses were arranged at random. An external controller 8 was connected to the air blower 9 by common electrical lines, and connected to the environment measurement apparatuses 7 by radio communication.

Each environment measurement apparatus 7 has, e.g., an arrangement as shown in FIG. 8. That is, the environment measurement apparatus 7 has an environment sensor 11 for measuring the temperature and humidity, a signal detector/processor 12 for detecting and processing signals form the environment sensor 11, a transmitter/receiver 13 for exchanging signals with the external controller 8, an antenna 14, a power supply 15, and a container 16 containing these components. The antenna 14 is used to perform normal electromagnetic wave communication using microwaves, and is sometimes unnecessary when optical communication is used. The environment sensor 11 typically has the structure shown in FIG. 1 or 2. The power supply 15 is a secondary battery such as a lithium ion battery, a fuel cell, a solar cell, or a device which externally radiates electromagnetic waves such as microwaves.

Referring to FIG. 10, the environment measurement apparatuses 7 and external controller 8 directly exchange signals by radio. However, it is naturally also possible to install a relay device between them. Also, the specifications of the signal detector/processor 12, transmitter/receiver 13, and antenna 14 can be determined in accordance with the application.

In the environment measurement system shown in FIG. 10, the way the air stream blown from the air blower 9 flows in the space 10 is observed by each environment measurement apparatus 7. The external controller 8 controls the air supply conditions and observation conditions. Although the environment measurement apparatuses 7 are arranged at random except for the apparatuses A to G, the relative positions and absolute positions of these apparatuses are determined by the external controller 8. The position determination method can be any method. For example, an optical camera or ultrasonic camera can be installed in each environment measurement apparatus 7 or in the space 10, or position measurement cameras can be attached on the walls of the space 10. In the open air, a GPS function using artificial satellites can be used.

In accordance with instructions from the external controller 8, an air stream whose temperature and humidity are controlled under arbitrary conditions is blown from the air blower 9, and the temperature and humidity in the space are measured by the environment measurement apparatuses 7 when a desired time has elapsed. The external controller 8 collects the measurement results and performs processing such as totalization. In this manner, it is possible to check the way the temperature and humidity in the space 10 change by the air blown from the air blower 9. That is, in the example shown in FIG. 10, a space in which the temperature and humidity are controlled is an ellipse, and this space in which the temperature and humidity are controlled expands, as the air blowing time increases, such that the long axis of the ellipse gradually extends.

The results of temperature and humidity measurements performed in the environment measurement system of this embodiment will be explained below.

In this environment measurement system shown in FIG. 10, the environment measurement apparatuses 7 and external controller 8 are essential components. In this example, the space 10 to be measured had an area of 1,500 m$^2$ and a height of 10 m. Although an arbitrary number of environment measurement apparatuses 7 can be arranged in arbitrary positions, in this measurement 36 measurement apparatuses were used and environment measurement apparatuses corresponding to A to G in FIG. 10 were arranged at equal intervals (6 m) from the front surface of the air blower 9. Air having a controlled temperature and humidity blown from the air blower 9 was supplied at an air flow of a maximum of 5 m$^3$/min. Also, this air blown from the air blower 9 was supplied at a divergence angle of 20° in the directions indicated by the arrows X in FIG. 10 from a 50 cm×2 m air blow hole at 3 m from the floor. A personal computer was used as the external controller 8.

In this environment measurement system, information from each environment measurement apparatus 7 was collected by the personal computer 8 with the air blower 9 stopped. After that, air at a temperature of 25° C. and a humidity of 90% RH was blown at an air flow of 3 m$^3$/min from the air blower 9. The temperature and humidity were measured by each environment measurement apparatus 7, thereby observing changes in temperature and humidity in the space 10.

For example, the environment measurement apparatus A measured a temperature of 19.7° C. and a humidity of 40% RH before air was blown, and measured a temperature of 21° C. and a humidity of 60% RH when 1 minute elapsed after the start of air blow. The environment measurement apparatus D measured a temperature of 20.3° C. and a humidity of 48% RH. Also, when 10 minutes elapsed after the start of air blow, the environment measurement apparatus A measured a temperature of 23° C. and a humidity of 70% RH, and the environment measurement apparatus F measured a temperature of 21.3° C. and a humidity of 55% RH. Furthermore, by reading out information from each environment measurement apparatus at an arbitrary time by the personal computer, it was possible to check the temperature and humidity distributions in the spaces indicated by the ellipses in FIG. 10, and to check changes with time in a specific place.

The present invention can be applied to a system constituted by a plurality of devices, or to an apparatus comprising a single device. Furthermore, it goes without saying that the invention is applicable also to a case where the object of the invention is attained by supplying a program to a system or apparatus.

As many apparently widely different embodiments of the present invention can be made without departing from the spirit and scope thereof, it is to be understood that the invention is not limited to the specific embodiments thereof except as defined in the appended claims.

What is claimed is:

1. An environment sensor comprising:

a temperature sensor which measures a temperature; and
a humidity sensor which measures a humidity,
wherein said temperature sensor and humidity sensor are formed on the same substrate as a pair of stacked bodies having a multilayered structure including a lower electrode, a metal oxide layer formed on the lower electrode, and an upper electrode formed on the metal oxide layer,
the lower electrode of said temperature sensor and the lower electrode of said humidity sensor are common, and the upper electrode of said temperature sensor and the upper electrode of said humidity sensor are common,
of at least the upper electrode of the stacked bodies which faces a measurement ambient, the upper electrode of said temperature sensor covers a whole upper surface of the metal oxide layer, and the upper electrode of said humidity sensor partially covers the metal oxide layer, said humidity sensor measures the humidity by using a change in capacitance or electrical resistance between the electrodes, which is caused by water adsorbed by the metal oxide layer, the metal oxide layer covered by the upper electrode of said humidity sensor is formed by polycrystal structure, and the area of the metal oxide layer covered by the upper electrode of said humidity sensor is 50% or less of whole area of the metal oxide layer.

2. The sensor according to claim 1, wherein the metal oxide layer of at least said temperature sensor contains a material selected from the group consisting of a ferroelectric and pyroelectric.

3. The sensor according to claim 2, wherein the metal oxide has a perovskite structure.

4. The sensor according to claim 1, wherein at least one of a portion of said substrate in a formation region of said temperature sensor and a portion of said substrate in a formation region of said humidity sensor is removed.

5. An apparatus for measuring an environment, comprising:

an environment sensor including a temperature sensor which measures a temperature, and a humidity sensor which measures a humidity, said temperature sensor and humidity sensor being formed on the same substrate as a pair of stacked bodies having a multilayered structure including a lower electrode, a metal oxide layer formed on the lower electrode, and an upper electrode formed on the metal oxide layer, and said pair of stacked bodies being connected in series, of at least the upper electrode of the stacked bodies which faces a measurement ambient, the upper electrode of said temperature sensor covers a whole upper surface of the metal oxide layer, and the upper electrode of said humidity sensor partially covers the metal oxide layer, said humidity sensor measures the humidity by using a change in capacitance or electrical resistance between the electrodes, which is caused by water adsorbed by the metal oxide layer, the metal oxide layer covered by the upper electrode of said humidity sensor is formed by polycrystal structure, and the area of the metal oxide layer covered by the upper electrode of said humidity sensor is 50% or less of whole area of the metal oxide layer;

a signal detecting/processing unit which detects and processes an output signal from said environment sensor; and a transmitting unit which transmits an output processing result from said signal detecting/processing unit to an external apparatus by radio.

6. An environment measurement system comprising:

at least one environment measurement apparatus according to claim 5 arranged at an arbitrary position in an arbitrary space; and a unit which collects a measurement result from said environment measurement apparatus and performs predetermined processing, thereby measuring distributions of a temperature and humidity in the space and changes in temperature and humidity with time.

* * * * *